United States Patent [19]

Kawabata et al.

[11] Patent Number: 4,889,934
[45] Date of Patent: Dec. 26, 1989

[54] ORGANIC MIXED COMPLEX

[75] Inventors: Takeo Kawabata, Hirakata; Masahiko Miyashita, Takatsuki; Akira Taisha, Ibaraki, all of Japan

[73] Assignee: Nippon Gohsei Kagaku Kogyo Kabushiki Kaisha, Osaka, Japan

[21] Appl. No.: 147,407

[22] Filed: Jan. 26, 1988

[30] Foreign Application Priority Data

Jan. 27, 1987 [JP] Japan .................. 62-16358

[51] Int. Cl.$^4$ .......................... C07D 217/10
[52] U.S. Cl. .................. 546/151; 546/181; 546/347; 546/182; 548/335
[58] Field of Search ............. 546/151, 181, 182, 347; 548/335

[56] References Cited

FOREIGN PATENT DOCUMENTS 61-204173  9/1986  Japan .
61-254561 11/1986  Japan .

OTHER PUBLICATIONS

Matsunaga et al., "Chemical Abstracts", Vol. 86, 1977, Col. 86:24821v.
Ashwell et al., "Chemical Abstracts", Vol. 86, 1977, Col. 86:131565m.
Murakami et al., (I), "Chemical Abstracts", Vol. 87, 1987; Col. 87:125917g.
Mihaly et al., "Chemical Abstracts", Vol. 87, 1987, Col. 160389h.
Ashwell et al. (II), "Chemical Abstracts", Vol. 87, 1987, Col. 87:175897w.
Murakami et al. (II), "Chemical Abstracts", Vol. 88, 1978, Col. 88: 181278g.
Miljak et al., "Chemical Abstracts", Vol. 88, 1978, Col. 88:202031p.

*Primary Examiner*—Glennon H. Hollrah
*Assistant Examiner*—James H. Turnipseed
*Attorney, Agent, or Firm*—Armstrong, Nikaido, Marmelstein, Kubovcik & Murray

[57] ABSTRACT

Novel organic mixed complexes are provided which have the general formula

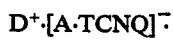

wherein $D^+$ is an N-alkylonium cation derived from a nitrogen-containing hetercyclic compound (D) selected from the group consisting of pyridines, quinolines, isoquinolines and imidazoles and $[A \cdot TCNQ]^-$ is an anion radical derived from a 2,5-bis[(alkoxycarbonyl)-ethyl]-7,7,8,8-tetracyanoquinodimethane (A) of the formula

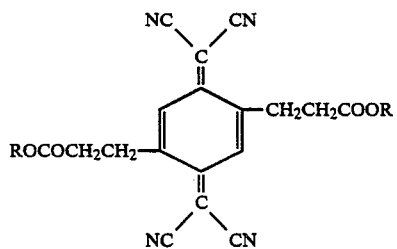

in which R is an alkyl group containing 1-10 carbon atoms, and 7,7,8,8-tetracyanoquinodimethane (TCNQ).

2 Claims, No Drawings

ORGANIC MIXED COMPLEX

BACKGROUND OF THE INVENTION

This invention relates to a novel organic mixed complex composed of 7,7,8,8-tetracyanoquinodimethane (hereinafter referred to as TCNQ) plus a certain derivative of TCNQ as the acceptor and an N-alkyl nitrogen-containing heterocyclic compound as the donor.

Electroconductive organic compounds are characterized in that they are light in weight, show anisotropy, can be processed or shaped with ease and can undergo chemical modification. Therefore, they are currently attracting much attention.

Typical of such electroconductive organic compounds are TCNQ complexes composed of nitrogen-containing heterocyclic compounds on one hand and TCNQ on the other. Among the relevant references, there may be mentioned "Synthesis and Application of Organic Semiconductor Materials", published by K.K. C.M.C., 1981, and "Gendai Kagaku (Modern Chemistry)", published by K.K. Tokyo Kagaku Dojin, No. 141, pages 12–19, 1982.

A Japanese patent application laid open under Kokai No. 254561/86 discloses a TCNQ complex composed of a nitrogen-containing heterocyclic compound cation, TCNQ anion radical and neutral TCNQ.

A Japanese patent application laid open under Kokai No. 204173/86 discloses a 1:1 or 1:2 complex between a specific 7-membered nitrogen-containing heterocyclic compound and TCNQ.

However, the above-mentioned TCNQ complexes each has a relatively high melting point (for example, the 1:2 complex between such nitrogen-containing heterocyclic compound and TCNQ generally has a melting point above 200° C.), hence processing or shaping thereof is subject to restriction, although they have high electroconductivity. Accordingly, it is highly desirable to develop electroconductive organic compounds lower in melting point.

Under these circumstances, the present invention has been completed as a result of searching for organic complexes lower in melting point as compared with the prior art TCNQ complexes.

SUMMARY OF THE INVENTION

The invention thus provides novel organic mixed complexes of the general formula

wherein the constituent $D^+$ is an N-alkylonium cation derived from a nitrogen-containing heterocyclic compound (D) selected from the group consisting of pyridines, quinolines, isoquinolines and imidazoles and the constituent $[A \cdot TCNQ]^-$ is an anion radical derived from a 2,5-bis[(alkoxycarbonyl)ethyl]-7,7,8,8-tetracyanoquinodimethane (A) of the general formula

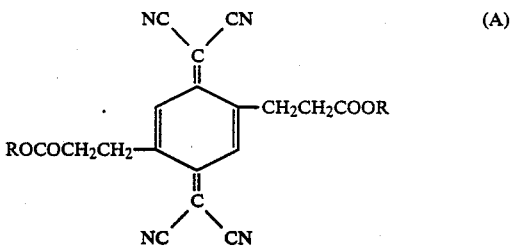

wherein R is an alkyl group containing 1–10 carbon atoms, and 7,7,8,8-tetracyanoquinodimethane (TCNQ).

DETAILED DESCRIPTION OF THE INVENTION

Compound (A)

The 2,5-bis[(alkoxycarbonyl)ethyl]-7,7,8,8-tetracyanoquinodimethane (A), which is defined by the above formula, is a novel compound not yet described in the literature, which has the skeleton of TCNQ and for which Japanese Pat. Applications Nos. 166081/85 (Kokai No. 26260/87) and 256255/86 are pending.

Referring to the compound (A) mentioned above, R is an alkyl group and examples of said alkyl group are alkyl groups containing 1–10 carbon atoms, such as methyl, ethyl, propyl, butyl, amyl, hexyl, octyl, decyl and cyclohexyl. The two alkyl groups in the above formula may be different but should preferably be the same from the easy production viewpoint. Industrially, the use of a lower alkyl group containing about 1–4 carbon atoms is practical.

The above compound (A), when the two R's are each a methyl group, for instance, shows a melting point of 168° C. and is fairly soluble in methanol and other general-use solvents. For comparison, TCNQ has a melting point of about 294°–296° C. and is soluble only in several solvents such as acetonitrile, dioxane and dimethylformamide. It is insoluble in most of other organic solvents.

The above compound (A) can be produced by oxidizing a 2,5-bis(dicyanomethylene)cyclohexane-1,4-ylene-(3-proionic acid alkyl ester) of the general formula

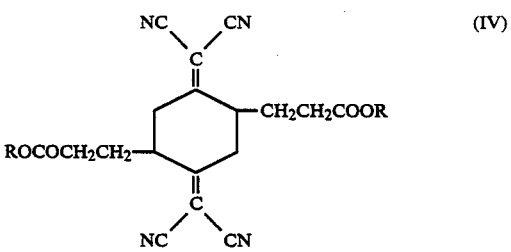

wherein R is as defined above.

The oxidation reaction is carried out in an inert gas atmosphere and generally in a medium such as acetonitrile, using N-bromosuccinimide or bromine as the oxidizing agent. A base such as pyridine is caused to exist in the reaction system.

For said reaction, a reaction temperature of 0° C. to 80° C. and a reaction period of about 0.1–8 hours are sufficient.

Generally, N-bromosuccinimide or bromine is used in an amount of 1–5 moles per mole of the compound (IV).

After completion of the reaction, water is added to the reaction system as necessary. The resultant precipitate is collected and purified in the conventional manner.

The compound (A) can also be produced by oxidizing a 2,5-bis(dicyanomethylene)cyclohexane-1,4-ylene-(3-propionic acid) (IVa) and esterifying the resulting 2,5-bis(carboxyethyl)-7,7,8,8-tetracyanoquinodimethane. The esterification is carried out by a per se known method, for example by converting the oxidation product to the corresponding acid chloride by treatment with thionyl chloride, for instance, and then reacting said acid chloride with an alcohol. The esterification reaction may be effected simultaneously during the oxidation reaction by carrying out the oxidation reaction in the presence of an alcohol.

The compound (IV) or (IVa), which is the starting material for the production of the compound (A), can be prepared, for example, by the method described in Japanese Patent Application No. 166081/85 (Kokai No. 26260/87) as follows:

A dialkyl succinylsuccinate of the general formula

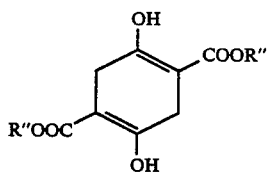
(I)

wherein R″ is an alkyl group, is reacted with acrylic acid or an alkyl acrylate of the general formula

CH$_2$=CHCOOR‴ wherein R‴ is a hydrogen atom or an alkyl group, to give a cyclohexane-2,5-dione derivative of the general formula

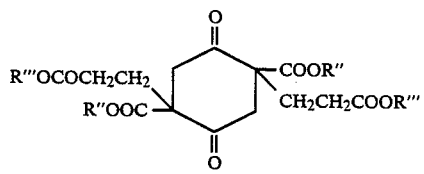
(II)

The reaction is generally carried out in an organic solvent in the presence of a metal alcoholate catalyst.

The above cyclohexane-2,5-dione derivative (II) is then heated in an aqueous medium in the presence of a strong acid such as hydrochloric acid, sulfuric acid, p-toluenesulfonic acid or a strong acid form ion exchange resin, to give cyclohexane-2,5-dione-1,4-ylene-(3-propionic acid) of the formula

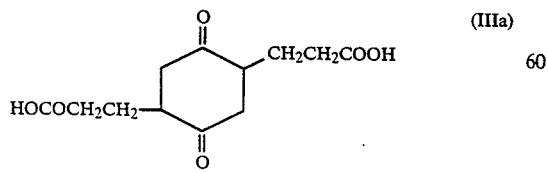
(IIIa)

Esterification of this compound (IIIa) gives a cyclohexane-2,5-dione-1,4-ylene-)3-propionic acid alkyl ester) (III).

The subsequent reaction of the compound (III) with malononitrile gives the corresponding 2,5-bis(dicyanomethylene)cyclohexane-1,4-ylene-(3-propionic acid alkyl ester) (IV).

Alternatively, the compound (IV) can also be produced by reacting the above compound (IIIa) first with malononitrile and then esterifying the resulting 2,5-bis(dicyanomethylene)cyclohexane-1,4-ylene-(3-propionic acid) (IVa).

Furthermore, the compound (IV) or (IVa), which is the starting material for the compound (A), is also producible by the method described in Japanese Pat. Application No. 256255/86.

Thus, cyclohexane-1,4-dione is enaminated with pyrrolidine and the resulting 1,4-dipyrrolidinocyclohexane-1,3-diene is then reacted with acrylic acid or an acrylic ester to give the compound (IIIa) or (III).

These reactions are carried out as follows:

The enamine formation reaction with pyrrolidine in the first step converts cyclohexane-1,4-dione to 1,4-dipyrrolidinocyclohexane-1,3-diene.

Benzene, toluene or xylene, for instance, is used as a solvent.

The reaction temperature is preferably a refluxing temperature. The byproduct water formed during the reaction is continuously removed from the reaction system for allowing the reaction to proceed. The use of a catalyst is not essential but an acid such as p-toluenesulfonic acid can be used.

Advantageously, the reaction system is maintained under a nitrogen atmosphere so that the oxidation of the product enamine can be inhibited.

The quantity of pyrrolidine is selected within the range of 2-4 moles per mole of cyclohexane-1,4-dione.

A period of 1-3 hours is suitable as the reaction time.

After removal of the solvent and residual pyrrolidine from the first step reaction mixture, the second step reaction with the unsaturated compound (acrylic acid or acrylate ester) is carried out.

Usable solvents are dioxane, dimethylformamide, ethanol, methanol and acetonitrile, among others.

The unsaturated compound is used in an amount of 2-4 moles per mole of cyclohexane-1,4-dione.

The reaction is conducted under reflux for about 3-24 hours. Then, after addition of water in an amount of about 2 molar equivalents relative to cyclohexane-1,4-dione, 1,4-dione, hydrolysis is conducted under reflux for about 1-2 hours, whereby the compound (IIIa) or (III) is obtained.

The method of converting the compound (IIIa) or (III) to the compound (IV) is the same as mentioned hereinbefore.

TCNQ

TCNQ can be produced in the conventional manner, for example by reacting cyclohexane-1,4-dione with malonitrile, followed by oxidation with N-bromosuccinimide or bromine.

N-Alkylonium cation (D+)

The nitrogen-containing heterocyclic compound (D) is selected from the group consisting of pyridines, quinolines, isoquinolines, and imidazoles.

The reaction of this nitrogen-containing heterocyclic compound (D) with an alkyl iodide or bromide gives the corresponding N-alkylonium cation (D+), namely an N-alkylpyridinium cation, N-alkylquinolinium cation, N-alkylisoquinolinium cation or N- alkylimidazolium cation, in the halide state. Such N-alkylonium cations are represented by the following skeletal formula:

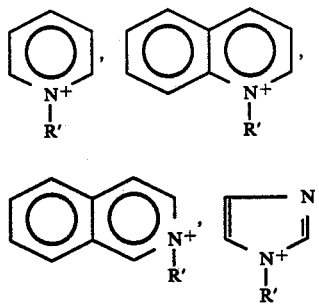

In the above formulas, R' is an alkyl group containing about 1–10 carbon atoms, such as a methyl, ethyl, n-propyl, isopropyl, n-butyl, isobutyl, sec-butyl, amyl, hexyl or octyl group. Particularly preferred as the group R' is an alkyl group containing 1–4 carbon atoms.

Organic mixed complex

The organic mixed complex according to the invention is composed of two constituents, namely the N-alkylonium cation (D+) corresponding to the above-mentioned nitrogen-containing heterocyclic compound (D) and the anion radical

derived from the above-mentioned compound (A) and TCNQ, and is represented by the general formula

This mixed complex can suitably be produced by the following methods:

(a) A warmed solution of a complex of the formula D+·TCNQ⁻ in a solvent is mixed with a warmed solution of the compound (A) in a solvent and, after cooling, the resulting crystals are collected, washed as necessary, and dried.

(b) A warmed solution of a complex of the formula D+·A⁻ in a solvent is mixed with a warmed solution of TCNQ in a solvent and, after cooling, the resulting crystals are collected, washed as necessary, and dried.

(c) A warmed solution of D+ in a solvent is mixed with a warmed solution of the compound (A) in a solvent and a warmed solution of TCNQ in a solvent and, after cooling, the resulting crystals are collected, washed as necessary, and dried.

Said complex of the formula D+·TCNQ⁻ or D+·A⁻ can be prepared, for example, as follows:

(i) A warmed solution of an N-alkylonium iodide or bromide in a solvent is mixed with a warmed solution of the compound (A) in a solvent and, after cooling, the resulting crystals are collected, washed as necessary, and dried.

(ii) A warmed solution of an N-alkylonium iodide or bromide in a solvent is mixed with a warmed solution of the lithium complex of TCNQ or compound (A) in a solvent and, after cooling, the resulting crystals are collected, washed as necessary, and dried.

Usable as the solvent for reaction and/or washing in the above-mentioned process (a), (b), (c), (i) or (ii) are organic solvents, such as alcohols (methanol, ethanol, n-propanol, isopropanol, etc.), ketones (acetone, methyl ethyl ketone, etc.), nitriles (acetonitrile, etc.), esters (methyl acetate, ethyl acetate, etc.), ethers (dimethyl ether, tetrahydrofuran, etc.), hydrocarbons (hexane, etc.) and cellosolve. Such organic solvents are used either alone or in combination of two or more. The solvents may contain water. Whereas the solvents for TCNQ are limited to acetonitrile, tetrahydrofuran and a few others, the compound (A) is soluble in solvents in general use and this fact broadens the range of solvent selection therefor.

In spite of the fact that its constituents are all organic compounds, the thus-formed mixed complex is highly electroconductive. Therefore, said complex is useful as or in manufacturing electroconductive paint, electroconductive ink, electroconductive plastic material, electroconductive rubber, high-function electroconductive molecular membrane, electrode, liquid crystal display tube, solar cell, high-density memory, nonlinear optical material, biological element, solid electrolyte and condenser, among others.

Thus the reaction between D+·TCNQ⁻ and compound (A), the reaction between D+·A⁻ and TCNQ or the reaction among D+, A and TCNQ gives the mixed complex

whose constituents are the N-alkylonium cation (D+) and the anion radical [A·TCNQ]⁻ corresponding to the above-mentioned compound (A) plus TCNQ.

This mixed complex is a complex of the charge transfer type and shows good electroconductivity.

The novel organic mixed complex according to the invention has a very low melting point while maintaining the high electroconductivity of the corresponding prior art TCNQ complex. Therefore, said mixed complex has markedly improved processability and shapability (or moldability).

Accordingly, various applications that cannot be expected of the conventional TCNQ complexes can be expected of the organic mixed complex according to the invention as an electroconductive material, among others.

EXAMPLES

The following examples are further illustrative of the present invention.

Production of compound (A)

A mixture of 128.13 g (0.5 mole) of diethyl succinylsuccinate (I), 112.4 g (1.0 mole) of methyl acrylate, 2.18 g (0.04 mole) of sodium methylate and 700 ml of methanol was refluxed in an argon atmosphere for 15 hours. Then, the methanol was distilled off under reduced pressure, a small quantity of water with benzene added thereto was added to the residue and, after phase separation, the benzene layer was dried and then distilled under reduced pressure to give 181.97 g of the cyclohexane-2,5-dione derivative (II) as a yellowish brown oil.

A mixture of 177.55 g (0.414 mole) of the cyclohexane-2,5-dione derivative (II) obtained as described above, 300 ml of water and 10 g of concentrated sulfuric acid was refluxed. Since the boiling point lowered with the progress of the reaction, the methanol and ethanol were distilled off from time to time. After 120 hours of refluxing, the methanol and ethanol then remaining in the reaction mixture were distilled off and the residual reaction mixture was cooled.

The resultant crystalline precipitate was collected by filtration, whereby 29.98 g of a crude product melting at 190° C. was obtained. Recrystallization from water gave cyclohexane-2,5-dione-1,4-ylene-(3-propionic acid) (IIIa) melting at 192°–194° C.

A solution of 12.8 g (50 millimoles) of cyclohexane-2,5-dione-1,4-ylene-(3-propionic acid) (IIIa) obtained as described above in 300 ml of water was neutralized with an equivalent quantity of sodium hydrogen carbonate, then 6.6 g (100 millimoles) of malononitrile and 1.0 g of β-alanine were added, and the mixture was heated on a water bath for 2 hours, then cooled and made acidic with diluted hydrochloric acid. The resultant crystalline precipitate was collected by filtration, washed and dried to give 8.6 g of 2,5-bis(dicyanomethylene)cyclohexane-1,4-ylene-(3-propionic acid) (IVa).

2,5-Bis(dicyanomethylene)cyclohexane-1,4-ylene-(3-propionic acid) (IVa) (8.6 g) obtained as described above was dissolved in methanol, then 31.0 g of thionyl chloride was added at 10° C., and the mixture was stirred for 2 hours. The resultant crystals were collected by filtration, washed and dried to give 8.3 g of 2,5-bis-(dicyanomethylene) cyclohexane-1,4-ylene-(3-propionic acid methyl ester) (IV).

2,5-Bis(dicyanomethylene)cyclohexane-1,4-ylene-(3-propionic acid methyl ester) (IV) (5.7 g) obtained as described above was suspended in 500 ml of acetonitrile and, after argon substitution, 6.0 g of N-bromosuccinimide was added. The resultant mixture was stirred for 1 hour. After cooling, 9.0 g of pyridine was added and the mixture was stirred for 2 hours while the temperature of the system was maintained at 10° C. or below. Then, 300 ml of water was added, and the resultant precipitate was collected by filtration, washed with water and dried to give 5.1 g of the desired compound. The yield was 90% based on 2,5-bis (dicyanomethylene)cyclohexane-1,4-ylene-(3-propionic acid methyl ester) (IV).

This compound had the following characteristics and was identified as 2,5-bis[(methoxycarbonyl)ethyl]7,7,8,8-tetracyanoquinodimethane (A-1) of the formula:

[Chemical structure: NC\C/CN double bond to cyclohexadiene ring with CH$_2$CH$_2$COOCH$_3$ and CH$_3$OCOCH$_2$CH$_2$ substituents, and =C(CN)$_2$ group]

Melting point: 167°–168° C.

IR, ν cm$^{-1}$ (KBr): 3050, 2960, 2215, 1740, 1550, 1515, 1200, 1175, 915, 900.

NMR, δ ppm (CDCl$_3$): 7.33 (2H, s), 3.70 (6H, s), 3.33 (4H, t), 2.73 (4H, t).

Mass spectrum, m/e : 376, 345, 344, 317, 303, 259, 258 (B), 257.

Oxidation of 2,5-bis(dicyanomethylene)cyclohexane-1,4-ylene-(3-propionic acid ethyl ester) (IV) gave 2,5bis[(ethoxycarbonyl)ethyl]-7,7,8,8-tetracyanoquinodimethane (A-2).

Similarly, oxidation of 2,5-bis(dicyanomethylene)-cyclohexane-1,4-ylene-(3-propionic acid propyl ester) (IV) gave 2,5-bis[(propioxycarbonyl)ethyl]-7,7,8,8-tetracyanoquinodimethane (A-3).

TCNQ

TCNQ obtained by reaction of cyclohexane-1,4-dione with malononitrile and the subsequent oxidation with N-bromosuccinimide or bromine was used.

N-Alkylonium iodide (D$^+$I$^-$)

The following N-alkylonium iodides (D$^+$I$^-$) were obtained by reacting pyridine, quinoline, isoquinoline or 2-phenyl imidazole with an equimolar amount of methyl iodide, ethyl iodide, n-propyl iodide, isopropyl iodide or n-butyl iodide:

D−1+I−: N-Methylpyridinium iodide,
D−2+I−: N-n-Butylpyridinium iodide,
D−3+I−: N-Ethylquinolinium iodide,
D−4+I−: N-Isopropylquinolinium iodide,
D−5+I−: N-Ethylisoquinolinium iodide,
D−6+I−: N-n-Propylisoquinolinium iodide,
D−7+I−: N-n-Butylisoquinolinium iodide, and
D−8+I−: 3-n-Butyl-2-phenylimidazolium iodide.

EXAMPLES 1–12

Mixed complexes were produced by one of the methods (a) and (b) mentioned below using the above-mentioned compounds (A) and TCNQ in combination with the above-mentioned N-alkylonium iodides (D$^+$I$^-$.)

First, the lithium complex of compound (A) or TCNQ was dissolved in ethanol with warming, a solution of an equimolar amount of an N-alkylonium iodide (D$^+$I$^-$) in acetonitrile as prepared by dissolution with warming was added, and the mixture was allowed to cool to and stand at room temperature. The resultant crystalline precipitate was collected by filtration, washed with ethanol and dried under vacuum to give the complex D$^+$·A$^-$ or D$^+$·TCNQ$^-$.

(a) An acetonitrile solution of the complex D$^+$·TCNQ$^-$ obtained as described above and an acetonitrile solution of an equimolar amount of the compound (A) were mixed together each in a warmed state. The mixture was allowed to cool to and stand at room temperature. The resultant crystalline precipitate was collected by filtration, washed with acetonitrile and dried under vacuum to give the corresponding mixed complex.

(b) An acetonitrile solution of the complex D$^+$·A$^-$ obtained as described above was mixed with an acetonitrile solution of an equimolar amount of TCNQ in a warmed condition, and the mixture was then cooled. The resultant crystalline precipitate was collected by filtration, washed with acetonitrile and dried under vacuum to give the corresponding mixed complex.

The characteristics of the mixed complexes thus obtained are shown in Table 1.

For comparison, the melting points and resistivities of the 1:2 complexes of the corresponding nitrogen-containing heterocyclic compounds and TCNQ as obtained by the conventional method are also shown in Note 2 to Table 1.

The resistivity values were determined by pressure molding of each mixed complex by the conventional method, resistance measurement by the two-terminal method and calculation using the equation:

Resistivity (Ω·cm) = resistance (Ω) × electrode contact area (cm$^2$)/specimen thickness (cm)

TABLE 1

| Example | Mixed complexes | Method of production | Yield (%) | Appearance | Melting point (°C.) | Resistivity (Ω · cm) | Chemical formula | Elemental analysis C (%) | H (%) | N (%) |
|---|---|---|---|---|---|---|---|---|---|---|
| 1 | D-7$^+$ · [A-1 · TCNQ]$^{-}$ | (a) | 23.2 | Black-purple needles | 153–155 | 10.5 | $C_{45}H_{36}N_9O_4$ | 70.5 / 70.4 | 4.73 / 4.90 | 16.4 / 16.6 |
| 2 | D-7$^+$ · [A-1 · TCNQ]$^{-}$ | (b) | 31.4 | Black-purple needles | 153–155 | 13.0 | $C_{45}H_{36}N_9O_4$ | 70.5 / 70.9 | 4.73 / 4.21 | 16.4 / 16.9 |
| 3 | D-6$^+$ · [A-1 · TCNQ]$^{-}$ | (b) | 41.0 | Black-purple needles | 160–165 | 18.3 | $C_{44}H_{34}N_9O_4$ | 70.2 / 70.3 | 4.55 / 4.81 | 16.7 / 17.0 |
| 4 | D-5$^+$ · [A-1 · TCNQ]$^{-}$ | (b) | 42.3 | Black-purple needles | 167–172 | 15.3 | $C_{43}H_{32}N_9O_4$ | 69.9 / 70.3 | 4.36 / 4.43 | 17.1 / 17.6 |
| 5 | D-4$^+$ · [A-1 · TCNQ]$^{-}$ | (b) | 70.5 | Black-purple needles | 175–178 | 17.4 | $C_{44}H_{34}N_9O_4$ | 70.2 / 70.6 | 4.55 / 5.02 | 16.7 / 16.3 |
| 6 | D-3$^+$ · [A-1 · TCNQ]$^{-}$ | (b) | 38.5 | Black-purple needles | 164–169 | 35.6 | $C_{43}H_{32}N_9O_4$ | 69.9 / 70.0 | 4.36 / 4.01 | 17.1 / 17.6 |
| 7 | D-2$^+$ · [A-1 · TCNQ]$^{-}$ | (b) | 27.3 | Black-purple needles | 140–146 | 30.1 | $C_{41}H_{34}N_9O_4$ | 68.7 / 69.0 | 4.78 / 4.90 | 17.6 / 17.8 |
| 8 | D-1$^+$ · [A-1 · TCNQ]$^{-}$ | (b) | 47.0 | Black-purple needles | 173–180 | 14.8 | $C_{38}H_{28}N_9O_4$ | 67.6 / 67.8 | 4.18 / 4.19 | 18.7 / 19.1 |
| 9 | D-5$^+$ · [A-1 · TCNQ]$^{-}$ | (b) | 51.1 | Black-purple needles | 175–180 | 3.8 | $C_{45}H_{36}N_9O_4$ | 70.5 / 70.8 | 4.73 / 4.98 | 16.4 / 16.7 |
| 10 | D-1$^+$ · [A-1 · TCNQ]$^{-}$ | (b) | 22.9 | Black-purple needles | 190–220 | 9.5 | $C_{40}H_{33}N_9O_4$ | 68.4 / 68.9 | 4.58 / 4.26 | 17.9 / 18.2 |
| 11 | D-5$^+$ · [A-1 · TCNQ]$^{-}$ | (b) | 41.5 | Black-green crystals | 160–180 | 6.3 | $C_{47}H_{40}N_9O_6$ | 71.0 / 71.4 | 5.07 / 5.19 | 15.9 / 15.6 |
| 12 | D-8$^+$ · [A-1 · TCNQ]$^{-}$ | (b) | 25.9 | Black crystals | 250–260 | 53.7 | $C_{43}H_{31}N_{12}$ | 72.0 / 71.8 | 4.36 / 4.85 | 23.5 / 23.3 |

(Note 1)
In elemental analysis columns, the upper row values are theoretical ones while lower row values are found ones.

(Note 2)
For D-7$^+$ · (TCNQ)$_2^{-}$, the melting point is 210–220° C. and the resistivity is 14 Ω · cm.
For D-6$^+$ · (TCNQ)$_2^{-}$, the melting point is 210–220° C. and the resistivity is 36 Ω · cm.
For D-5$^+$ · (TCNQ)$_2^{-}$, the melting point is 210–220° C. and the resistivity is 25 Ω · cm.
For D-4$^+$ · (TCNQ)$_2^{-}$, the melting point is 225–235° C. and the resistivity is 35 Ω · cm.
For D-3$^+$ · (TCNQ)$_2^{-}$, the melting point is 237–239° C. and the resistivity is 25 Ω · cm.
For D-1$^+$ · (TCNQ)$_2^{-}$, the melting point is 249–280° C. and the resistivity is $1.2 \times 10^3$ Ω · cm.

What is claimed is:

1. A organic mixed complex of the formula

D$^+$·[A·TCNQ]$^-$ wherein D$^+$ is an N-alkylonium cation of a nitrogen-containing heterocyclic compound (D) selected from the group consisting of pyridines, quinolines, isoquinolines and imidazoles, and [A·TCNQ]$^-$ is an anion radical of 2,5-bis[(alkoxycarbonyl)ethyl]-7,7,8,8-tetracyanoquinodimethane (A) of the formula

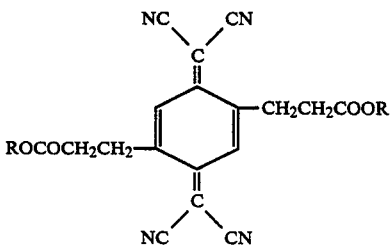

in which R is an alkyl group containing 1–10 carbon atoms, and 7,7,8,8-tetracyanoquinodimethane (TCNQ).

2. An organic mixed complex as claimed in claim 1, wherein the group R in said 2,5-bis[(alkoxycarbonyl)ethyl]-7,7,8,8-tetracyanoquinodimethane (A) is a lower alkyl group having 1–4 carbon atoms.

* * * * *